US011826338B2

(12) United States Patent
Berthoud et al.

(10) Patent No.: US 11,826,338 B2
(45) Date of Patent: *Nov. 28, 2023

(54) METHODS FOR TREATING OBESITY

(71) Applicant: Board Of Supervisors Of Louisiana State University And Agricultural And Mechanical College, Baton Rouge, LA (US)

(72) Inventors: Hans-Rudolf Berthoud, Baton Rouge, LA (US); Frank L. Greenway, Baton Rouge, LA (US); Stefany DePrato Primeaux, Baton Rouge, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/371,838

(22) Filed: Jul. 9, 2021

(65) Prior Publication Data

US 2021/0330632 A1 Oct. 28, 2021

Related U.S. Application Data

(62) Division of application No. 16/713,831, filed on Dec. 13, 2019, now Pat. No. 11,058,662, which is a division of application No. 15/750,575, filed as application No. PCT/US2016/046352 on Aug. 10, 2016, now Pat. No. 10,507,194.

(60) Provisional application No. 62/203,119, filed on Aug. 10, 2015.

(51) Int. Cl.
| | | |
|---|---|---|
| *A61K 36/00* | (2006.01) | |
| *A61K 31/337* | (2006.01) | |
| *A61K 36/185* | (2006.01) | |
| *A61K 31/365* | (2006.01) | |
| *A61P 3/04* | (2006.01) | |

(52) U.S. Cl.
CPC .......... *A61K 31/337* (2013.01); *A61K 31/365* (2013.01); *A61K 36/185* (2013.01); *A61P 3/04* (2018.01)

(58) Field of Classification Search
CPC ........................................................ A61P 3/04
See application file for complete search history.

(56) References Cited

U.S. PATENT DOCUMENTS

| | | |
|---|---|---|
| 8,617,689 B2 | 12/2013 | Chen et al. |
| 2005/0025823 A1 | 2/2005 | Fong et al. |
| 2006/0135471 A1 | 6/2006 | Bailly et al. |

FOREIGN PATENT DOCUMENTS

| | | |
|---|---|---|
| JP | 2005187432 | 7/2005 |
| KR | 2011049060 | 5/2011 |
| WO | WO2014/102776 | 7/2014 |

OTHER PUBLICATIONS

Afifi et al, Chemical composition and in vitro studies of the essential oil and aqueous extract of Pelargonium graveolens growing in Jordan for hypoglycaemic and hypolipidemic properties. European Journal of Medicinal Plants (2014), vol. 4, No. 2, pp. 220-233 (Year: 2014).*
Ackroff et al. "Effects of the lipase inhibitor orlistat on intake and preference for dietary fat in rats", Am J Physiol. 271(1 Pt 2):R48-54 (1996) (Abstract Only).
Dubin et al, The Effect of Modified Sham Feeding With Orlistat in Overweight and Obese Subjects: A Pilot Study: Journal of Investigative Medicine, (Feb. 2013) vol. 61, No. 2, pp. 397 (Year: 2013).
Kawai et al. "Importance of lipolysis in oral cavity for orosensory detection of fat", Am J. Physiol Regul Integr Comp Physiol 285:R447-R454 (2003).
Little et al. "Effects of dietary fat on appetite and energy intake in health and obesity—Oral and gastrointestinal sensory contributions", Physiology & Behavior 104:613-620 (2011).
Notification Concerning Transmittal of International Preliminary Report on Patentability corresponding to International Application No. PCT/US2016/046352 dated Feb. 22, 2018.
Notification of Transmittal of the International Search Report and the Written Opinion of the International Searching Authority, or the Declaration corresponding to International Application No. PCT/US2016/046352 dated Dec. 1, 2016.
Ullrich et al. "Impact of carbohydrate and fat intake on weight-reducing efficacy of orlistat", Aliment Pharmacol Ther. 17(8):1007-13 (2003) (Abstract Onlyu).

* cited by examiner

*Primary Examiner* — Qiuwen Mi
(74) *Attorney, Agent, or Firm* — Baker, Donelson, Bearman, Caldwell & Berkowitz, PC

(57) ABSTRACT

The present invention relates to methods of treating overweight or obesity, reducing fat, sugar, and food intake, and reducing body weight or body weight gain in a subject using geranium oil or orlistat mouthwash, or a combination of both.

5 Claims, 4 Drawing Sheets

METHODS FOR TREATING OBESITY

STATEMENT OF PRIORITY

This application is a divisional of U.S. patent application Ser. No. 16/713,831, which issued as U.S. Pat. 11,058,662 on Jul. 13, 2020, which is a division of U.S. patent application Ser. No. 15/750,575, which issued as U.S. Pat. No. 10,507,194 on Dec. 17, 2019, which is a 35 U.S.C. § 371 national phase application of PCT/US2016/046352, filed on Aug. 10, 2016, which claims the benefit of U.S. Provisional Application Ser. No. 62/203,119, filed Aug. 10, 2015, the contents of which are incorporated by reference herein in their entireties.

FIELD OF THE INVENTION

The present invention relates to methods of treating overweight or obesity and reducing weight gain and food intake in a subject using orlistat mouthwash and/or geranium oil.

BACKGROUND OF THE INVENTION

Obesity is worldwide health problem that is reaching epidemic proportions. Since 1980 the worldwide prevalence of obesity has more than doubled. As of 2014 the World Health Organization estimates that over 600 million adults are obese, comprising about 13% of the world's adult population. Overweight and obesity are the fifth leading risk for global deaths.

Obesity is a complex disease influenced by genetics, diet, exercise, and a complex biology. Typical treatments are diet and exercise, however such behavior modification is not efficacious in the long run for a significant portion of patients. While bariatric surgery to reduce the size of the stomach (gastric bypass surgery) is an effective treatment for causing weight loss in morbidly obese people, it is invasive, expensive and can have significant side effects. Current therapeutics leave much to be desired. Orlistat, which blocks fat absorption in the gut, is one drug approved by the FDA for the long-term treatment of obesity. However, side effects associated with orlistat administration, including oily spotting, oily fecal discharge, fecal urgency, and fecal incontinence, limit its appeal. Thus, development of improved obesity treatments are urgently needed.

SUMMARY OF THE INVENTION

The present invention provides effective and convenient methods for treatment or prevention of overweight or obesity and to help people reduce body weight and/or food intake. Methods utilizing both geranium oil and orlistat mouthwash have been demonstrated to be beneficial.

Thus, one aspect of the present invention is directed to a method for reducing dietary fat intake in a subject in need thereof, comprising administering to the subject a mouthwash composition comprising a therapeutically effective amount of orlistat; thereby reducing dietary fat intake.

In another aspect the present invention is directed to a method for reducing dietary sugar intake in a subject in need thereof, comprising administering to the subject a composition for oral administration comprising a therapeutically effective amount of geranium oil, thereby reducing dietary sugar intake.

In a further aspect the present invention is directed to a method for treating overweight or obesity in a subject in need thereof, comprising administering to the subject a mouthwash composition comprising a therapeutically effective amount of orlistat, thereby treating overweight or obesity.

In an additional aspect the present invention is directed to a method for reducing body weight or body weight gain in a subject in need thereof, comprising administering to the subject a mouthwash composition comprising a therapeutically effective amount of orlistat, thereby reducing body weight.

In another aspect the present invention is directed to a method for reducing food intake in a subject in need thereof, comprising administering to the subject a mouthwash composition comprising a therapeutically effective amount of orlistat, thereby reducing food intake.

In a further aspect the present invention is directed to a method for treating overweight or obesity in a subject in need thereof, comprising administering to the subject a composition for oral administration comprising a therapeutically effective amount of geranium oil, thereby treating overweight or obesity.

In an additional aspect the present invention is directed to a method for reducing body weight or body weight gain in a subject in need thereof, comprising administering to the subject a composition for oral administration comprising a therapeutically effective amount of geranium oil, thereby reducing body weight.

In another aspect the present invention is directed to a method for reducing food intake in a subject in need thereof, comprising administering to the subject a composition for oral administration comprising a therapeutically effect amount of geranium oil, thereby reducing food intake.

In a further aspect the present invention is directed to a method for reducing dietary fat intake and/or dietary sugar intake in a subject in need thereof, comprising administering to the subject: a) a composition comprising a therapeutically effective amount of geranium oil; and b) a composition comprising a therapeutically effective amount of orlistat, thereby reducing dietary fat intake and/or dietary sugar intake.

In an additional aspect the present invention is directed to a method for reducing food intake in a subject in need thereof, comprising administering to the subject: a) a composition for oral administration comprising a therapeutically effective amount of geranium oil; and b) a mouthwash composition comprising a therapeutically effective amount of orlistat, thereby reducing food intake.

In another aspect the present invention is directed to a method for reducing body weight or body weight gain in a subject in need thereof, comprising administering to the subject: a) a composition for oral administration comprising a therapeutically effective amount of geranium oil; and b) a mouthwash composition comprising a therapeutically effective amount of orlistat, thereby reducing body weight.

In an a further aspect the present invention is directed to a method for treating overweight or obesity in a subject in need thereof, comprising administering to the subject: a) a composition for oral administration comprising a therapeutically effective amount of geranium oil; and b) a mouthwash composition comprising a therapeutically effective amount of orlistat, thereby treating overweight or obesity.

In an additional aspect the present invention is directed to a mouthwash composition comprising orlistat in an amount effective to treat overweight or obesity in a subject.

In another aspect the present invention is directed to a composition for oral administration comprising geranium oil in an amount effective to treat overweight or obesity in a subject.

These and other aspects of the invention are set forth in more detail in the description of the invention below.

DETAILED DESCRIPTION OF THE INVENTION

Figure 1:
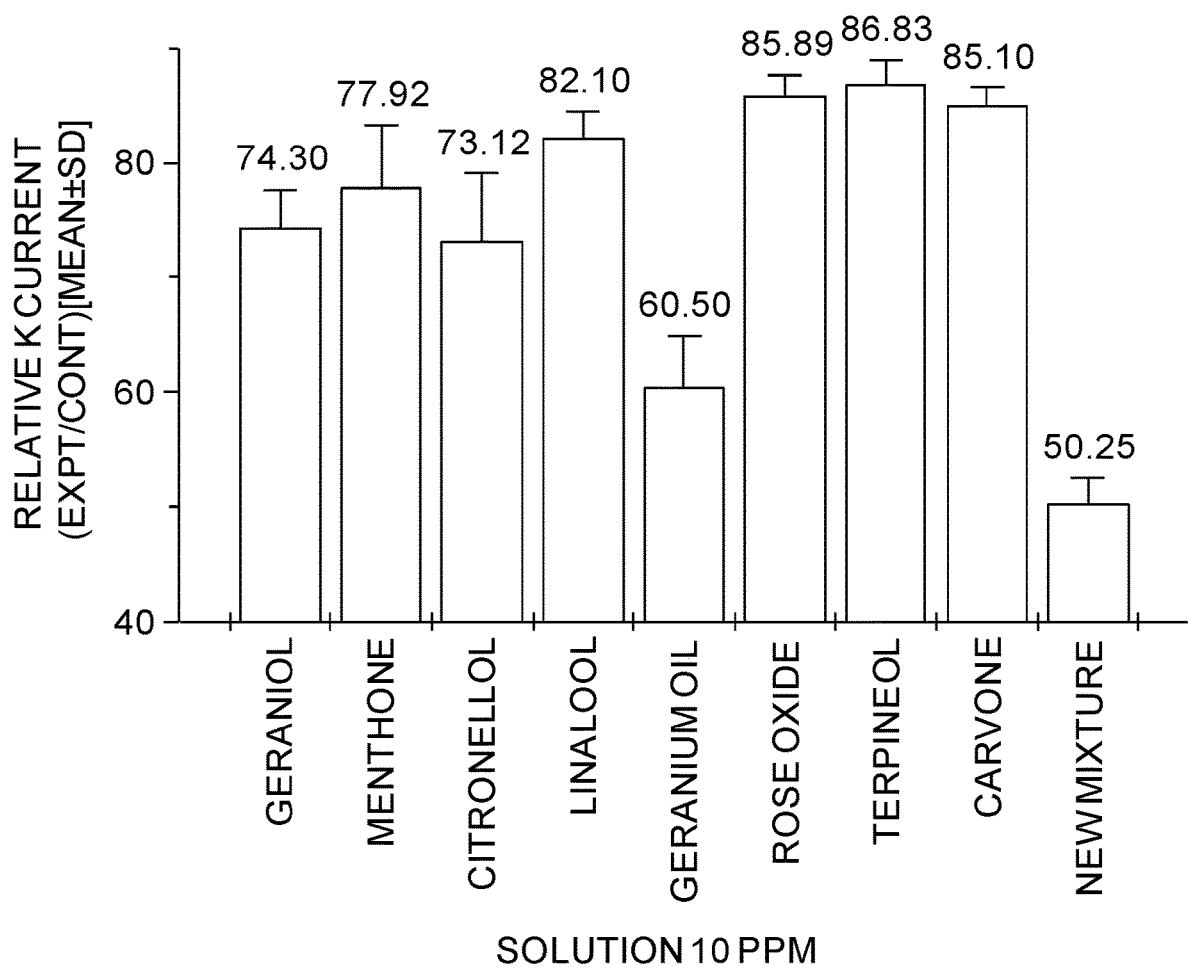
FIG. 1 shows the results for a patch clamp assay on rodent taste bud cells determining inhibition of taste receptors on the tongue by geranium oil.

The present invention now will be described hereinafter with reference to the accompanying examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, patent publications and other references cited herein are incorporated by reference in their entireties for the teachings relevant to the sentence and/or paragraph in which the reference is presented.

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim or the description of this invention is not intended to be interpreted to be equivalent to "comprising."

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more.

An "effective" amount as used herein is an amount that provides a desired effect.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

By the terms "treat," "treating," or "treatment," it is intended that the severity of the subject's condition is reduced or at least partially improved or modified and that some alleviation, mitigation or decrease in at least one clinical symptom is achieved.

As used herein the term "body weight gain" refers to the increase in weight of a subject's body over time.

As used herein the term "food intake" refers to the intake of calories in any form, including without limitation, food and drink delivered orally or enterally.

The phrase "treating overweight or obesity," as used herein encompasses alleviating, mitigating, or decreasing at least one clinical symptom of overweight or obesity or slowing of progression of the clinical symptoms.

The term "mouthwash" as used herein refers to a liquid solution that is used by a subject to rinse the mouth then is spit out without significant amounts of the mouthwash being swallowed (e.g., less than about 10%, 5%, or 1%).

As used herein the term "obesity" refers to a body mass index (BMI) between 30 and 40 in adult humans.

For people under 20 "obesity" is defined as a BMI above the 95th percentile compared to people of the same age in the US who participated in the national surveys that were conducted from 1963-65 to 1988 to 94. As used herein, the term can include both obesity and morbid obesity.

As used herein the term "overweight" refers to a BMI between 25 and 30 in adult humans.

The term "simultaneously" refers to actions occurring at the same time or within about one minute of each other.

The term "sequentially" refers to actions in a sequence or a series of events. As used herein, the term refers to administration of one active agent after another, e.g., within about 60 minutes of each other.

The present invention provides effective and convenient methods for treatment or prevention of overweight or obesity and to help people reduce body weight and/or food intake. Both geranium oil and orlistat mouthwash have been demonstrated to be beneficial.

The present invention is based in part on the discovery that an effective amount of geranium oil can suppress appetite and food intake. Without being limited by mechanism, it is thought that taste receptors on the tongue are inhibited and those in the mucosa of the small intestine, including the duodenum, are activated by an effective amount of geranium oil, thereby suppressing appetite and food intake.

Geranium oil is an extract from *Pelargonium graveolens*, a species native to South Africa, Zimbabwe and Mozambique. Common names include "rose geranium" and "old fashioned rose geranium." Geranium oil is a hydrophobic liquid containing multiple species of organic compounds. It is an "essential oil," meaning that the extract has captured the "essence" of the plant. Essential oils are often extracted by distillation, using steam. Other methods include solvent extraction. Geranium oil is commercially available.

A therapeutically effective amount of geranium oil can be delivered via any suitable method known in the art. In one embodiment, the geranium oil is delivered orally, e.g., in a capsule. Suitable delivery vehicles include, without limitation, geranium oil in an acid resistant capsule, a water soluble dry form of geranium oil, and a water soluble dry form contained in an acid resistant capsule. In any delivery vehicle the geranium oil can be diluted about 1:100 to about 1:10,000, e.g., about 1:100, 1:250, 1:500, 1:1000, 1:2000, 1:3000, 1:4000, 1:5000, or any range therein. Suitable diluents include, without limitation, water, physiologic saline, oils, other essential oils, creams, and other liquids and semi-solids.

In some embodiments, a therapeutically effective amount of geranium oil may be delivered prior to a meal. Prior to a meal means immediately before eating, e.g., within about 1, 2, 3, 4, 5, 6, 7, 8, 9, 10, 20, 30, 45, 60, 75, 90, 105, 120, 135, 150, 165, or 180 minutes prior to eating. In other embodiments, geranium oil may be taken before, during and/or after a meal. In other embodiments, a therapeutically effective amount of geranium oil is delivered on a regular schedule, e.g., 1, 2, 3, 4, or 5 times a day.

Another aspect of the present invention is based in part on the discovery that an effective amount of orlistat mouthwash prior to consumption of a fatty meal decreases food and fat calorie intake in fat preferring people by approximately 20%. Without being limited by mechanism, it is thought that orlistat mouthwash inhibits lingual lipase thereby blocking the generation of free fatty acids from triglyceride hydrolysis. Fatty acids in the mouth are thought to signal the taste for fat through taste receptors to the brain. Abrogating this signal has a satiating effect thereby reducing fat intake. Administering orlistat as mouthwash provides beneficial effects without known side effects associated with capsules, including oily spotting, oily fecal discharge, fecal urgency, and fecal incontinence.

A therapeutically effective amount of orlistat can be delivered via any suitable mouthwash composition known in the art. In one embodiment, the orlistat is delivered in an aqueous mouthwash comprising water and optionally additional components such as salts, buffers, viscosity modifiers, flavorants, colorants, etc.

A therapeutically effective amount of orlistat mouthwash contains about 1 mg to about 200 mg of orlistat per dose, e.g., about 1, 5, 10, 20, 30, 40, 50, 60, 70, 80, 90, 100, 110, 120, 130, 140, 150, 160, 170, 180, 190, or 200 mg or any range therein. In some embodiments, the dose may be even higher, e.g., about 500 or 1000 mg or more as the majority of the dose may not be absorbed during the time the mouthwash is in contact with the oral mucosa.

A therapeutically effective amount of orlistat mouthwash may be administered prior to a meal. Prior to a meal means immediately before eating, e.g., within about 1, 2, 3, 4, 5, 6, 7, 8, 9, 10, 20, 30, 45, 60, 75, 90, 105, 120, 135, 150, 165, and 180 minutes prior to eating. In other embodiments, a therapeutically effective amount of orlistat mouthwash may be taken before, during, and/or after a meal. In other embodiments, a therapeutically effective amount of geranium oil is delivered on a regular schedule, e.g., 1, 2, 3, 4, or 5 times a day.

As used herein, the term "subject" refers to humans and other animals. Suitable subjects include mammals such as humans, as well as those mammals of importance due to being endangered, such as Siberian tigers; of economic importance, such as animals raised on farms; animals of social importance to humans, such as animals kept as pets or in zoos; and research animals, such as mice, rabbits, guinea pigs, ferrets, dogs, cats, monkeys, and apes. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; horses; and poultry. Human subjects include neonates, infants, juveniles, and adults. In some embodiments, the subject is an animal model of overweight or obesity. In some embodiments, the subject is a fat-preferring subject.

As used herein, the term "fat-preferring subject" refers to subjects that crave fat-sweet and/or fat-protein foods or subjects that prefer diets composed of fat levels above the percent fat typically found in the American diet (e.g., above about 35%).

In another aspect the present invention is directed to a method for treating overweight or obesity, a method for reducing body weight or body weight gain, a method for reducing food intake, and a method for reducing dietary fat intake and/or dietary sugar intake in a subject in need thereof, comprising administering to the subject: a) a composition for oral administration comprising a therapeutically effective amount of geranium oil, and b) a mouthwash composition comprising a therapeutically effective amount of orlistat.

The combination of orally administered geranium oil and an orlistat mouthwash has two advantages over using either separately. First, the combination may address both problems that lead to overweight or obesity, sweet or sugary foods and foods high in fat. By acting on both types of food, the combined impact of geranium oil and orlistat may reduce food intake to a greater degree, and be more effective in the treatment of overweight or obesity. Secondly, by using geranium oil and orlistat together, the combination that will be effective for subjects with either fat-sweet or fat-protein preferences. In certain embodiments, the combination of geranium oil and orlistat may have additive or synergistic effects on overweight or obesity, food intake, and/or weight loss.

A therapeutically effective amount of orlistat mouthwash and geranium oil can be administered simultaneously or sequentially prior to consumption of a meal. In other embodiments, the combination may be taken before, during, and/or after a meal. In other embodiments, the combination may be delivered on a regular schedule, e.g., 1, 2, 3, 4, or 5 times a day.

In another aspect the present invention is directed to any of the above disclosed combinations of orlistat and geranium oil. In one aspect, the invention is directed to a composition for oral administration comprising geranium oil in an amount effective to treat overweight or obesity in a subject. In one embodiment, said geranium oil is contained in an acid resistant capsule. In one embodiment, the geranium oil is in a water soluble dry form, e.g., in an acid resistant capsule. The geranium oil may be diluted about 1:100 to about 1:1000.

Another aspect the present invention is directed to a mouthwash composition comprising orlistat in an amount effective to treat overweight or obesity in a subject. In one embodiment, the orlistat mouthwash contains about 1 mg to about 120 mg orlistat per dose.

A further aspect the present invention is directed to a combination comprising the geranium oil composition of the invention and an orlistat mouthwash composition of the invention. The combination may be in the form of a kit. The geranium oil composition and orlistat mouthwash composition may be in separate containers. The combination or kit may further comprise other components, such as delivery devices, dosage measuring cups, etc.

The present invention is more particularly described in the following examples that are intended as illustrative only since numerous modifications and variations therein will be apparent to those skilled in the art.

Example 1

Activation of Duodenal Fatty Acid-Sensitive Taste Receptors by Geranium Oil

Figure 2A:
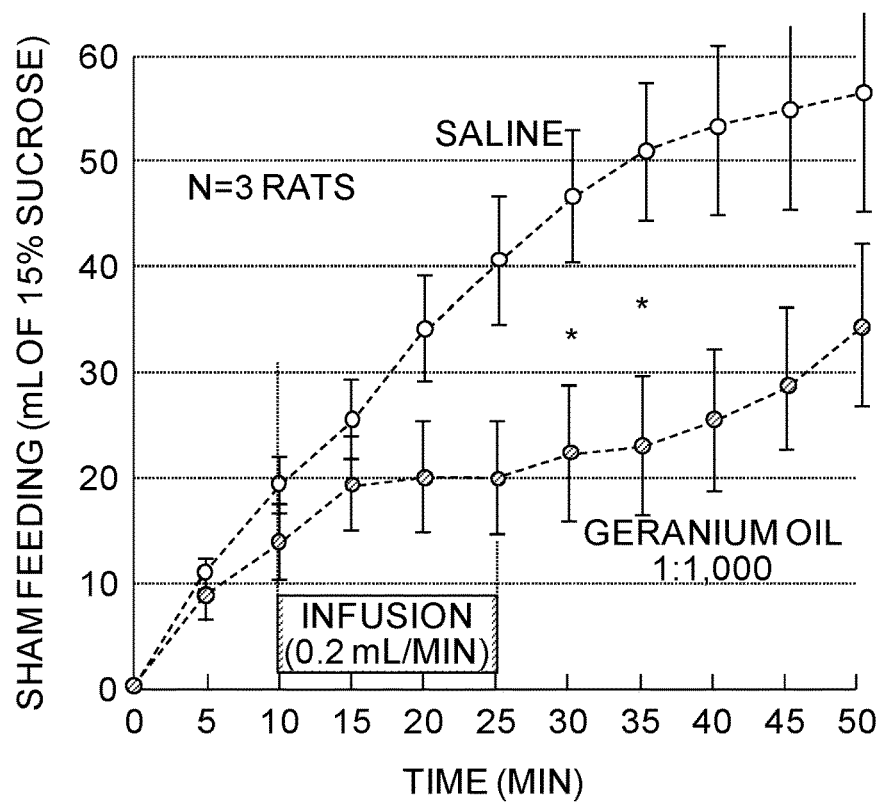
FIGS. 2A and 2B show the suppressing effect that activation of intestinal taste receptors has on appetite and food intake in sham feeding rats.
Figure 2B:
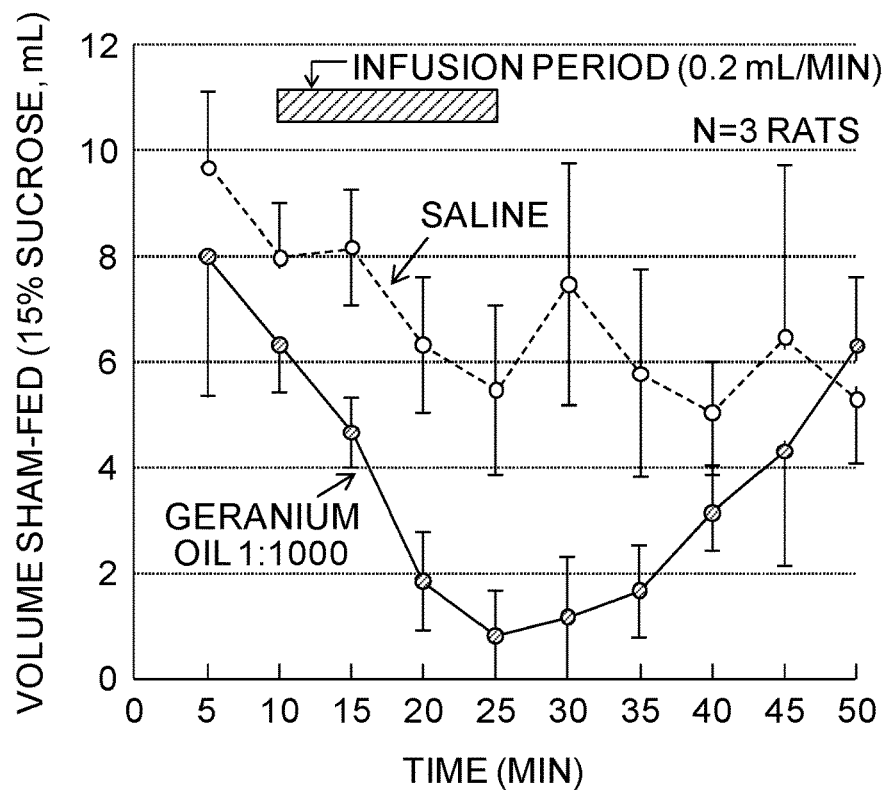

It was previously demonstrated that 10 ppm geranium oil inhibits the taste receptor on the tongue by 60.5% (FIG. 1). Importantly, it has been shown that similar fatty acid-sensitive taste receptors are present in the mucosa of the small intestine, including the duodenum. To demonstrate that activation of these intestinal taste receptor cells can suppress appetite and food intake, geranium oil or saline were infused directly into the duodenum of sham-feeding rats. A fistula was made from the stomach to the abdominal wall in a rat, so that the rat will continually drink a 15% sucrose solution that is collected through a tube. Geranium oil diluted 1:1000 in water was tested in 3 sham-fed rats (FIGS. 2A and 2B). The results showed that duodenal infusion at 0.2 mL/min of a geranium oil solution for 15 minutes significantly attenuated consumption of the 15% sucrose solution. These results demonstrate that geranium oil could reduce caloric intake and cause weight loss, if delivered to the duodenum in the correct concentration.

Example 2

Orlistat Mouthwash Decreases Food and Energy Intake

The effect of orlistat mouthwash (OM) on fat intake was determined by a double-blind, placebo controlled, randomized and balanced crossover study performed on 10 healthy individuals between 18 and 70 years of age and a body mass index (BMI) between 25 and 35 kg/m$^2$.

Figure 3A:
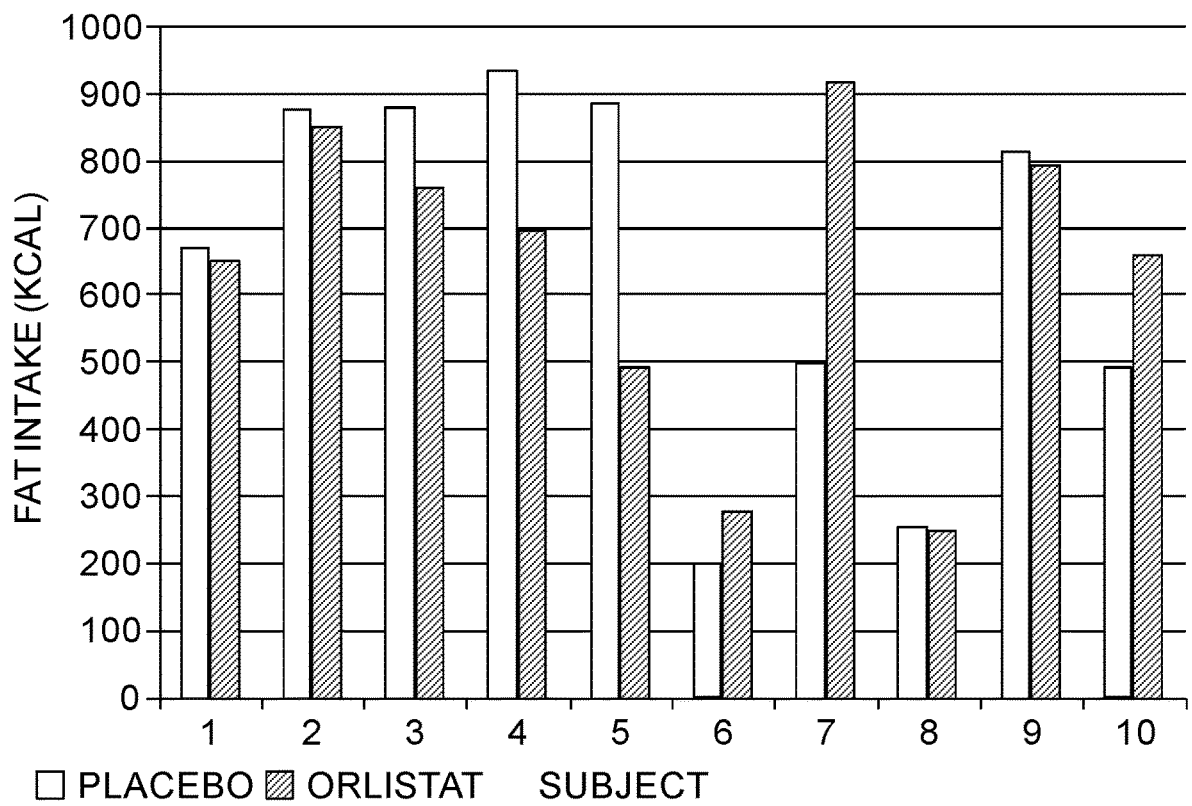
FIG. 3A shows the effects on total fat intake in 10 individuals who were administered orlistat mouthwash prior to a fatty meal.
Figure 3B:
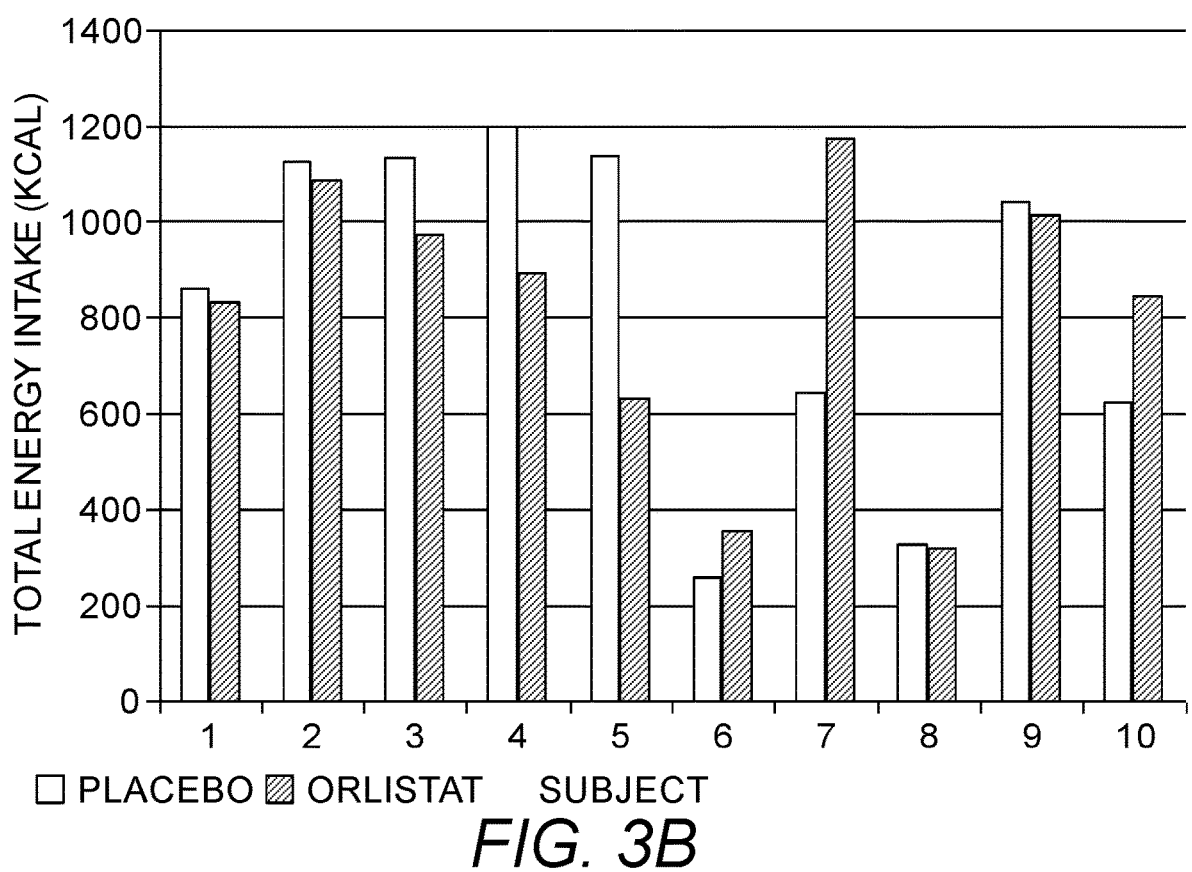
FIG. 3B shows the effects on total caloric intake in 10 individuals who were administered orlistat mouthwash prior to a fatty meal.

Prospective subjects were recruited during a screening visit in which they completed a medical questionnaire, a menstrual questionnaire to determine the ideal study period in females (luteal phase) and a 3-factor eating questionnaire (measuring dietary restraint, inhibition and hunger). Inclusion criteria included healthy male and females between 18-70 years of age with a BMI between 25-35 kg/m$^2$. Exclusions included pregnancy, a restraint score of greater than 13 or a significant aversion to the test food (as determined by a sample tasting). Also excluded were any subjects taking diabetic medications, systemic glucocorticoids or any agent that was known to cause weight or appetite changes. Approximately 1-2 minutes before eating, subjects swished approximately 2 teaspoons of OM (240 mg/10 mL) or a placebo solution in their mouth for 30 seconds before spitting out the solution. Subjects were then given the high-fat test meal (multiple servings of Johnsonville® Bratwurst: (21 grams of fat per serving)). Subjects were allowed to eat ad libitum for 20 minutes. Test meal contents were weighed before and after testing and determinations were made to calculate total caloric (energy) and total fat intake during the meal. (FIGS. 3A and 3B) Patients were their own controls. Fat intake and appetite ratings were compared using paired t-tests. Non-parametric data like adverse events were analyzed using the chi-squared test. Statistical significance was set at an alpha of 0.05. Subjects consumed 15.51±219.38 kcal less fat (FIG. 3A) and 20.14±279.81 kcal less total energy (FIG. 3B) following the OM compared to the placebo mouthwash.

Figure 3C:
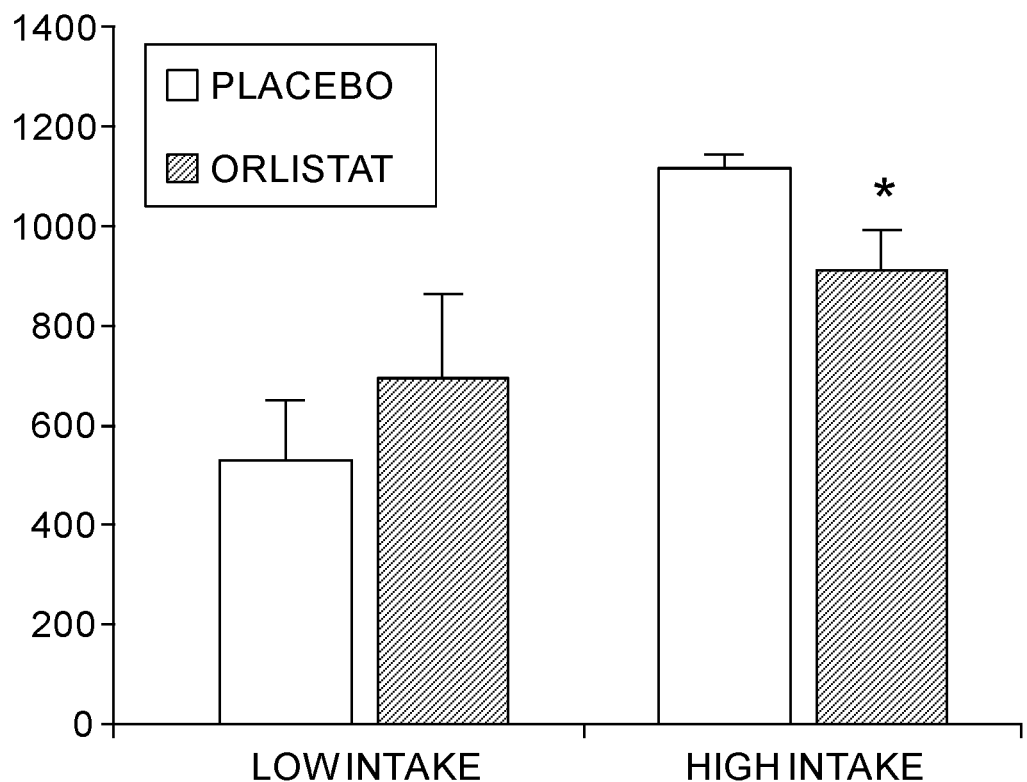
FIGS. 3C and 3D show the effects of orlistat mouthwash administered prior to a fatty meal on total fat intake in individuals who ate larger and smaller portions.
Figure 3D:
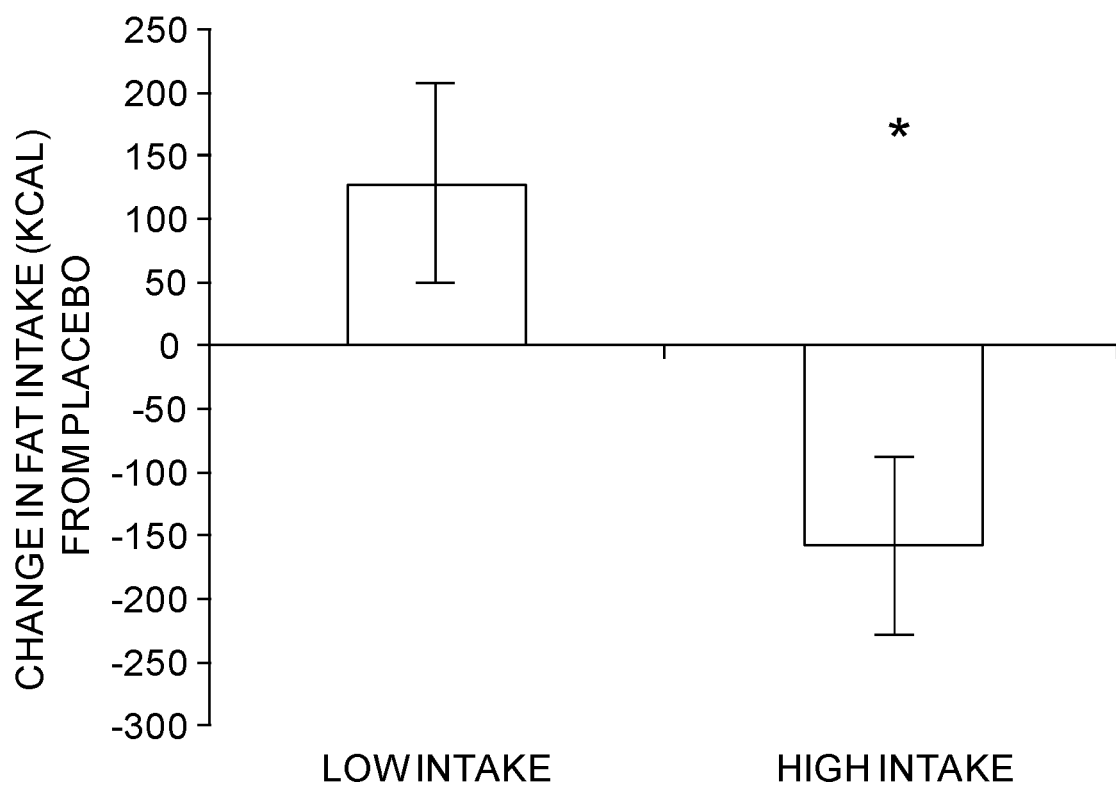

While treatment with OM did not significantly reduce food intake overall, among the high food intake (fat-preferring, i.e., those that ate an amount of sausage above the mean) individuals a statistically significant decrease was observed, both when measured as fold change in fat intake (FIG. 3C) and total intake (FIG. 3D). This suggests that OM may be especially effective in fat-preferring subjects.

The foregoing is illustrative of the present invention, and is not to be construed as limiting thereof. The invention is defined by the following claims, with equivalents of the claims to be included therein.

That which is claimed is:

1. A mouthwash composition for oral administration comprising orlistat and geranium oil, wherein said mouthwash composition comprises about 1 mg to about 200 mg orlistat, and wherein said mouthwash composition comprises a dilution of about 1:100 to about 1:10,000 of geranium oil.

2. The composition of claim 1, wherein the composition comprises orlistat in an amount effective to treat overweight or obesity in a subject, and wherein the composition comprises geranium oil in an amount effective to treat overweight or obesity in a subject.

3. A method for treating overweight or obesity in a subject in need thereof, the method comprising administering to the subject the composition of claim 1.

4. A method for reducing body weight or body weight gain in a subject in need thereof, the method comprising administering to the subject the composition of claim 1.

5. A method for reducing food intake in a subject in need thereof, the method comprising administering to the subject the composition of claim 1.

* * * * *